US009885193B2

United States Patent
Chen et al.

(10) Patent No.: US 9,885,193 B2
(45) Date of Patent: Feb. 6, 2018

(54) SYSTEMS AND METHODS FOR CONTROLLING CHLORINATORS

(76) Inventors: Patrick Chen, North Kingstown, RI (US); Douglas Sawyer, Seekonk, MA (US); Michael Nilsson, Attleboro, MA (US); Raymond Denkewicz, East Greenwich, RI (US)

( * ) Notice: Subject to any disclaimer, the term of this patent is extended or adjusted under 35 U.S.C. 154(b) by 445 days.

(21) Appl. No.: 13/562,128

(22) Filed: Jul. 30, 2012

(65) Prior Publication Data
US 2013/0105403 A1    May 2, 2013

Related U.S. Application Data

(60) Provisional application No. 61/513,316, filed on Jul. 29, 2011.

(51) Int. Cl.
*E04H 4/12* (2006.01)
*G01N 35/00* (2006.01)
(Continued)

(52) U.S. Cl.
CPC .......... *E04H 4/1281* (2013.01); *C02F 1/008* (2013.01); *C02F 1/4674* (2013.01);
(Continued)

(58) Field of Classification Search
CPC ............... C02F 1/4674; C02F 2103/42; C02F 2001/46138; C02F 1/46109;
(Continued)

(56) References Cited

U.S. PATENT DOCUMENTS

| 2,436,077 A | 2/1948 | Robertson |
| 2,644,700 A | 7/1953 | Woodling |
| (Continued) | | |

FOREIGN PATENT DOCUMENTS

WO    2011/009170 A1    1/2011

OTHER PUBLICATIONS

Written Opinion dated Dec. 19, 2012, issued in connection with International Application No. PCT/US12/48891.
(Continued)

*Primary Examiner* — Claire A Norris
(74) *Attorney, Agent, or Firm* — McCarter & English, LLP

(57) ABSTRACT

Systems and methods for controlling chlorinators for pools and spas are provided. A controller communicates with a processor positioned within a replaceable cell cartridge of a chlorinator, to allow for remote control and diagnosis of the chlorinator and/or cell cartridge. The cell cartridge stores, in non-volatile memory on board the cartridge, one or more parameters associated with the cartridge. The controller can obtain this information from the processor of the cell cartridge, and can use same to configure operation of the chlorinator. Information relating to remaining cell life can be updated by the controller and stored in the non-volatile memory of the cell cartridge. Electrical and software-based mechanisms are provided for ensuring operation of only compatible cell cartridges with the chlorinator. A system for remotely diagnosing errors associated with the chlorinator is also provided.

25 Claims, 11 Drawing Sheets

(51) Int. Cl.
  *G06F 15/00* (2006.01)
  *C02F 1/00* (2006.01)
  *C02F 1/467* (2006.01)
  *G05B 19/4093* (2006.01)
  *C02F 103/42* (2006.01)

(52) U.S. Cl.
  CPC . *G01N 35/00584* (2013.01); *G05B 19/40938* (2013.01); *G06F 15/00* (2013.01); *C02F 2103/42* (2013.01); *C02F 2201/006* (2013.01); *C02F 2209/006* (2013.01); *C02F 2209/008* (2013.01); *C02F 2209/02* (2013.01); *C02F 2209/06* (2013.01); *C02F 2209/40* (2013.01); *C02F 2209/445* (2013.01); *C02F 2303/04* (2013.01); *G05B 2219/31095* (2013.01); *G05B 2219/49302* (2013.01); *G05B 2219/49304* (2013.01); *Y02P 90/265* (2015.11)

(58) Field of Classification Search
  CPC ...... C02F 2001/46123; C02F 2209/005; C02F 2209/29; C02F 2201/006; E04H 4/1281
  USPC ........... 210/167.11, 85, 138, 143, 149, 198.1
  See application file for complete search history.

(56) References Cited

U.S. PATENT DOCUMENTS

| | | | |
|---|---|---|---|
| 3,632,498 A | 1/1972 | Beer | |
| 3,933,616 A | 1/1976 | Beer | |
| 4,100,052 A | 7/1978 | Stillman | |
| 4,107,452 A | 8/1978 | Razvi | |
| 4,214,971 A | 7/1980 | Heikel et al. | |
| 4,250,910 A | 2/1981 | King | |
| 4,290,873 A * | 9/1981 | Weaver | 204/230.2 |
| 4,774,977 A | 10/1988 | Cohen | |
| 5,124,032 A | 6/1992 | Newhard | |
| 5,217,261 A | 6/1993 | DeWitt et al. | |
| 5,221,444 A | 6/1993 | Silveri | |
| 5,228,964 A | 7/1993 | Middleby | |
| 5,247,710 A | 9/1993 | Carder et al. | |
| 5,254,226 A | 10/1993 | Williams et al. | |
| 5,279,748 A | 1/1994 | Hackett | |
| 5,314,589 A | 5/1994 | Hawley | |
| 5,326,481 A | 7/1994 | Alwerud | |
| 5,401,373 A | 3/1995 | Silveri | |
| 5,422,014 A | 6/1995 | Allen et al. | |
| 5,460,706 A | 10/1995 | Lisboa | |
| 5,498,333 A | 3/1996 | Canther | |
| 5,546,982 A | 8/1996 | Clark et al. | |
| 5,580,438 A | 12/1996 | Silveri | |
| 5,649,560 A | 7/1997 | Lenney et al. | |
| 5,695,644 A | 12/1997 | Buchanan et al. | |
| 5,730,861 A | 3/1998 | Sterghos et al. | |
| 5,752,282 A | 5/1998 | Silveri | |
| 5,759,384 A | 6/1998 | Silveri | |
| 5,810,999 A | 9/1998 | Bachand et al. | |
| 5,893,977 A | 4/1999 | Pucci | |
| 5,932,093 A | 8/1999 | Chulick | |
| 5,985,155 A | 11/1999 | Maitland | |
| 5,993,669 A | 11/1999 | Fulmer | |
| 6,007,693 A | 12/1999 | Silveri | |
| 6,096,202 A | 8/2000 | Fulmer | |
| 6,125,481 A | 10/2000 | Sicilano | |
| 6,126,810 A | 10/2000 | Fricker et al. | |
| RE37,055 E | 2/2001 | Silveri | |
| 6,200,487 B1 | 3/2001 | Denkewicz, Jr. et al. | |
| 6,210,566 B1 | 4/2001 | King | |
| 6,217,754 B1 | 4/2001 | Ros | |
| 6,221,257 B1 | 4/2001 | Grim | |
| 6,228,272 B1 | 5/2001 | Gola | |
| 6,235,188 B1 | 5/2001 | Nakamura et al. | |
| 6,238,553 B1 | 5/2001 | Lin | |
| 6,238,555 B1 | 5/2001 | Silveri et al. | |
| 6,270,680 B1 | 8/2001 | Silveri et al. | |
| 6,287,466 B1 | 9/2001 | Yassin | |
| 6,444,129 B1 | 9/2002 | Collins | |
| 6,620,315 B2 | 9/2003 | Martin | |
| 6,623,647 B2 | 9/2003 | Martin | |
| 6,749,759 B2 | 6/2004 | Denes et al. | |
| 6,756,907 B2 | 6/2004 | Holloway | |
| 6,761,827 B2 | 7/2004 | Coffey | |
| 6,814,095 B2 | 11/2004 | King | |
| 6,827,847 B1 | 12/2004 | Chauvier | |
| 6,895,307 B2 | 5/2005 | Gardner, Jr. | |
| 6,948,510 B2 | 9/2005 | King | |
| 7,014,753 B2 | 3/2006 | Holstein et al. | |
| 7,211,176 B2 | 5/2007 | Hin et al. | |
| 7,390,399 B2 | 6/2008 | Dennis, II et al. | |
| 7,393,450 B2 | 7/2008 | Silveri | |
| 7,402,252 B2 | 7/2008 | Kadlec et al. | |
| 7,472,434 B1 | 1/2009 | Moldthan et al. | |
| 7,507,323 B1 | 3/2009 | Eyal | |
| 7,641,868 B2 | 1/2010 | Jang | |
| 7,658,824 B2 | 2/2010 | Bremauer | |
| 7,695,613 B2 | 4/2010 | Doyle et al. | |
| 7,722,746 B1 | 5/2010 | Eyal | |
| 7,767,067 B2 | 8/2010 | Silveri | |
| 7,867,401 B2 | 1/2011 | Dennis, II et al. | |
| 7,879,208 B2 | 2/2011 | Wu et al. | |
| 7,901,620 B2 | 3/2011 | Taguchi et al. | |
| 8,075,751 B2 | 12/2011 | Xie et al. | |
| 8,123,956 B2 | 2/2012 | King et al. | |
| 2001/0010296 A1 | 8/2001 | Hirota et al. | |
| 2002/0035403 A1 | 3/2002 | Clark et al. | |
| 2002/0108913 A1 | 8/2002 | Collins | |
| 2002/0152036 A1 | 10/2002 | Martin | |
| 2003/0160005 A1 | 8/2003 | Martin | |
| 2003/0168389 A1 | 9/2003 | Astle et al. | |
| 2004/0050781 A1 | 3/2004 | Coffey et al. | |
| 2004/0204779 A1 | 10/2004 | Mueller et al. | |
| 2004/0206706 A1 | 10/2004 | Costa et al. | |
| 2004/0249579 A1 | 12/2004 | Centanni | |
| 2005/0009193 A1 | 1/2005 | Page | |
| 2005/0137118 A1 | 6/2005 | Silveri | |
| 2005/0222786 A1 | 10/2005 | Tarpo et al. | |
| 2006/0027463 A1 | 2/2006 | Lavelle et al. | |
| 2006/0060512 A1 | 3/2006 | Astle et al. | |
| 2006/0091002 A1 | 5/2006 | Hin et al. | |
| 2006/0097878 A1 | 5/2006 | Von Broembsen | |
| 2006/0113256 A1 | 6/2006 | Birkbeck | |
| 2006/0169647 A1 | 8/2006 | Doyle et al. | |
| 2006/0249400 A1 | 11/2006 | Bremauer | |
| 2006/0266682 A1 | 11/2006 | Kennedy et al. | |
| 2006/0283789 A1 | 12/2006 | Kadlec et al. | |
| 2006/0283808 A1 | 12/2006 | Kadlec et al. | |
| 2007/0061051 A1 | 3/2007 | Maddox | |
| 2007/0144911 A1 | 6/2007 | Pulis | |
| 2007/0154322 A1 | 7/2007 | Stiles et al. | |
| 2007/0158274 A1 | 7/2007 | King | |
| 2007/0181439 A1 | 9/2007 | Wu et al. | |
| 2007/0215531 A1 * | 9/2007 | Wawrla et al. | 210/101 |
| 2007/0244576 A1 | 10/2007 | Potucek et al. | |
| 2008/0039977 A1 | 2/2008 | Clark et al. | |
| 2008/0173574 A1 | 7/2008 | Silveri | |
| 2008/0212782 A1 | 9/2008 | Brettle et al. | |
| 2008/0237148 A1 | 10/2008 | Dennis et al. | |
| 2008/0264447 A1 | 10/2008 | Eyal | |
| 2008/0289706 A1 | 11/2008 | King et al. | |
| 2009/0060269 A1 | 3/2009 | Rhoads | |
| 2009/0212782 A1 | 8/2009 | Silveri | |
| 2009/0218296 A1 | 9/2009 | King et al. | |
| 2009/0266231 A1 | 10/2009 | Franzen et al. | |
| 2009/0282627 A1 * | 11/2009 | Porat | 15/1.7 |
| 2009/0294381 A1 | 12/2009 | Coffey et al. | |
| 2010/0018930 A1 | 1/2010 | King et al. | |
| 2010/0032355 A1 | 2/2010 | Andrews et al. | |
| 2010/0096260 A1 | 4/2010 | Xie et al. | |
| 2010/0096338 A1 | 4/2010 | De Wet et al. | |
| 2010/0101010 A1 | 4/2010 | McCague | |
| 2010/0187122 A1 | 7/2010 | Zolotarsky | |
| 2010/0206815 A1 | 8/2010 | Garusi et al. | |
| 2010/0250449 A1 * | 9/2010 | Doyle | C02F 1/4674 705/302 |

(56) References Cited

U.S. PATENT DOCUMENTS

| | | |
|---|---|---|
| 2010/0254825 A1 | 10/2010 | Stiles, Jr. et al. |
| 2010/0313964 A1 | 12/2010 | Hin et al. |
| 2011/0010835 A1 | 1/2011 | McCague |
| 2011/0048964 A1 | 3/2011 | Luebke et al. |
| 2011/0049060 A1 | 3/2011 | Uy |
| 2011/0062086 A1 | 3/2011 | Burns et al. |
| 2011/0073488 A1 | 3/2011 | Hsiang Lin |
| 2011/0290707 A1 | 12/2011 | Porat |
| 2013/0105372 A1 | 5/2013 | Chen et al. |
| 2013/0105373 A1 | 5/2013 | Chen et al. |
| 2013/0105403 A1 | 5/2013 | Chen |

OTHER PUBLICATIONS

International Search Report of the International Search Authority dated Dec. 19, 2012, issued in connection with International Application No. PCT/US12/48891.
International Search Report of the International Searching Authority dated Sep. 28, 2012, issued in connection with International Application No. PCT/US12/48888.
Written Opinion of the International Searching Authority dated Sep. 28, 2012, prepared in connection with International Application No. PCT/US12/48888.
"Clearwater In-Line Chlorinator Installation Instructions," Waterway Plastics, 2008.
"Jandy Installation and Operation Manual," Zodiac Pool Systems, Inc., 2010.
"Jandy UltraFlex 2 Installation and Maintenace Guide," Zodiac Pool Systems, Inc., 2009.
International Search Report of the International Search Authority dated Oct. 1, 2012, issued in connection with International Application No. PCT/US12/48874.
Written Opinion dated Oct. 1, 2012, issued in connection with International Application No. PCT/US12/48874.
Notification concerning transmittal of copy of International Preliminary Report on Patentability, dated Feb. 13, 2014, issued in connection with International Application No. PCT/US12/48874.
Hayward "Salt and Swim Installation Quick Start Guide", earliest known date May 28, 2012 (from waybackmachine.com).
Office Action dated Sep. 12, 2016, issued in connection with U.S. Appl. No. 13/561,836 (22 pages).
Office Action dated Feb. 14, 2017, issued in connection with U.S. Appl. No. 13/562,043 (19 pages).
Extended European Search Report dated Jul. 1, 2015, issued by the European Patent Office in connection with European Patent Application No. 12820744.6 (7 pages).
International Search Report of the International Searching Authority dated May 9, 2014, issued in connection with International Application No. PCT/US14/13390 (3 pages).
Written Opinion of the International Searching Authority dated May 9, 2014, issued in connection with International Application No. PCT/US14/13390 (8 pages).
International Preliminary Report on Patentability dated Aug. 2, 2016 issued in connection with International Application No. PCT/US14/13390 (9 pages).
Office Action dated Aug. 24, 2015, issued in connection with U.S. Appl. No. 13/561,836 (12 pages).
Office Action dated Mar. 31, 2015, issued in connection with U.S. Appl. No. 13/562,043 (13 pages).
Office Action dated Oct. 2, 2015, issued in connection with U.S. Appl. No. 13/562,043 (11 pages).
Patent Examination Report No. 1, dated May 13, 2016, issued in connection with Australian Application No. 2012290215 (4 pages).
Patent Examination Report No. 1, dated Jul. 29, 2016, issued in connection with Australian Application No. 2012290292 (3 pages).
Patent Examination Report No. 1, dated Sep. 16, 2016, issued in connection with Australian Application No. 2012290213 (5 pages).
Extended European Search Report dated Feb. 17, 2016, issued by the European Patent Office in connection with European Patent Application No. 12820228.0 (13 pages).
Office Action dated May 25, 2016, issued in connection with U.S. Appl. No. 13/561,836 (14 pages).
Office Action dated Jun. 22, 2016, issued in connection with U.S. Appl. No. 13/562,043 (16 pages).
Extended European Search Report dated May 7, 2015, issued by the European Patent Office in connection with European Patent Application No. 12820373.4 (5 pages).
Extended European Search Report dated Jun. 1, 2015, issued by the European Patent Office in connection with European Patent Application No. 12820744.6 (7 pages).
Extended European Search Report dated Oct. 26, 2015, issued by the European Patent Office in connection with European Patent Application No. 12820228.0 (6 pages).
Patent Examination Report No. 2, dated Jun. 22, 2017, issued in connection with Australian Application No. 2012290292 (5 pages).
International Search Report of the International Searching Authority dated Oct. 1, 2012, issued in connection with International Patent Application No. PCT/US12/48874 (4 pages).
Written Opinion of the International Searching Authority dated Oct. 1, 2012, issued in connection with International Patent Application No. PCT/US12/48874 (5 pages).
Patent Examination Report No. 2, dated Sep. 4, 2017, issued in connection with Australian Application No. 2012290213 (5 pages).
Patent Examination Report No. 3, dated Sep. 14, 2017, issued in connection with Australian Application No. 2012290213 (5 pages).
Office Action dated Oct. 4, 2017, issued in connection with U.S. Appl. No. 13/562,043 (26 pages).
Communication Pursuat to Article 94(3) dated Oct. 4, 2017, issued by the European Patent Office in connection with European Patent Application No. 12820373.4 (4 pages).
Office Action dated Nov. 20, 2017, issued in connection with U.S. Appl. No. 13/561,836 (29 pages).
Patent Examination Report No. 1, dated Nov. 17, 2017, issued in connection with Australian Application No. 2017203145 (4 pages).

* cited by examiner

SYSTEMS AND METHODS FOR CONTROLLING CHLORINATORS

RELATED APPLICATIONS

The present application claims the priority of U.S. Provisional Application Ser. No. 61/513,316 filed Jul. 29, 2011, the disclosure of which is expressly incorporated herein by reference in its entirety.

BACKGROUND

Technical Field

The present disclosure relates generally to equipment for sanitizing bodies of water such as pools and spas. More specifically, the present disclosure relates to systems and methods for controlling chlorinators.

Related Art

In the pool and spa field, it is important that water be adequately sanitized to prevent the growth of microorganisms, algae, etc. Adequate sanitization is important not only to protect the health and safety of bathers, but to also ensure proper water clarity in a pool or spa. A number of sanitization techniques have been implemented to sanitize pool/spa water, such as chemical additives (e.g., chlorine, bromine, etc.), introduction of ozone into pool/spa water, ultraviolet sanitization, etc.

Electrolytic cells (or, so-called "salt chlorinators") represent one way of sanitizing a pool or spa. In this arrangement, an amount of salt (sodium chloride) is periodically added to pool or spa water (e.g., a few times per year), an electric charge is imparted on the electrolytic cell, and pool or spa water is pumped through the cell. Through electrolysis, the salt in the water is converted to free chlorine, which is subsequently pumped into the pool or spa to sanitize water. One advantage to this approach is a reduction in the amount of chemicals that need to periodically be added to pool or spa water, in contrast to conventional chemical chlorination techniques which require frequent addition of dry or liquid chemicals to the pool/spa (e.g., by way of powder, tablets, etc.) in order to sanitize same.

Chlorinators having replaceable cell cartridges are known in the art. However, such systems do not include on-board electronic circuitry (including non-volatile memory) which stores operational and diagnostic information relating to the cell cartridge, so that proper operation and monitoring of the chlorinator can be carried out, e.g., by a controller in communication with the cell cartridge, or at a remote site (e.g., a manufacturer's facility) to which the cell cartridge can be shipped by the owner. Moreover, such systems do not include electrical and software-based security mechanisms to ensure usage of only compatible cartridges with the chlorinator.

Salt chlorinator systems that utilize replaceable chlorinator cartridges create a market for "knock-off" cell cartridges. This is primarily because a single chlorinator cartridge is designed for a single season of use, and therefore must be replaced at the beginning of each season. Knock-off cell cartridges not only have an economic impact, but can often create unsafe conditions. Specifically, only particular chlorinator cells should be used with specific chlorinator power supplies/controllers in order to ensure the safety of the system and the users. Standard connector systems allow knock-off companies to easily design cell cartridges to work with various chlorinators.

The present disclosure relates to systems and methods for controlling chlorinators, such as electrolytic chlorinators.

SUMMARY

The present disclosure relates to systems and method for controlling chlorinators for pools and spas, such as electrolytic chlorinators. The system includes a controller which communicates with a processor positioned within a replaceable cell cartridge of a chlorinator, to allow for remote control and diagnosis of the chlorinator and/or cell cartridge. The cell cartridge stores, in non-volatile memory on board the cartridge, one or more parameters associated with the cartridge, such as minimum/maximum electrical parameters, cell coating and/or life expectancy, thermal operating parameters, salinity operating parameters, etc. The controller can obtain this information from the processor of the cell cartridge, and can use same to configure operation of the chlorinator. Additionally, the processor of the cartridge can transmit operational status information in response to a request from the controller, such as current water temperature, flow rate, pH levels, etc., which information the processor can use to control the chlorinator. Information relating to remaining cell life can be updated by the controller and stored in the non-volatile memory of the cell cartridge. Electrical and software-based mechanisms are provided for ensuring operation of only compatible cell cartridges with the chlorinator. A system for remotely diagnosing errors associated with the chlorinator is also provided.

In one embodiment, a system for controlling a chlorinator is provided. The system includes a chlorinator including a body and a replaceable chlorinator cartridge removably positionable within said body, said chlorinator cartridge including a processor in electrical communication with a plurality of plates of the cartridge; and a controller in electrical communication with said chlorinator, said controller including a control panel for allowing a user to control operation of said chlorinator, wherein said processor of said chlorinator cartridge communicates with said controller to authenticate said replaceable cartridge, said controller prohibiting operation of said chlorinator cartridge if said chlorinator cartridge is not authenticated.

In another embodiment, a method for controlling a chlorinator is provided. The method includes the steps of establishing a communications link between a chlorinator and a controller; retrieving an authentication key from a non-volatile memory of a chlorinator cartridge removably positioned within said chlorinator; transmitting the authentication key from said chlorinator to said controller; processing the authentication key at the controller to determine whether the chlorinator cartridge is authenticated; and operating the chlorinator using the controller if the cartridge is authenticated by the controller.

In another embodiment, a method for diagnosing an error or a malfunction associated with pool or spa equipment is provided. The method includes the steps of displaying at a computer system a graphical user interface replicating at least one control panel of a piece of pool or spa equipment; allowing a user to replicate a control panel condition associated with the piece of pool or spa equipment using the graphical user interface; processing the replicated control panel condition using a diagnostic software engine to formulate a solution to the error or the malfunction; and conveying the solution to the error or the malfunction to the user using the computer system.

BRIEF DESCRIPTION OF THE DRAWINGS

The foregoing features of the invention will be apparent from the following Detailed Description, taken in connection with the accompanying drawings, in which.

DETAILED DESCRIPTION

The present disclosure relates to systems and methods for controlling chlorinators, as discussed in detail below in connection with FIGS. 1-13.

Figure 1:
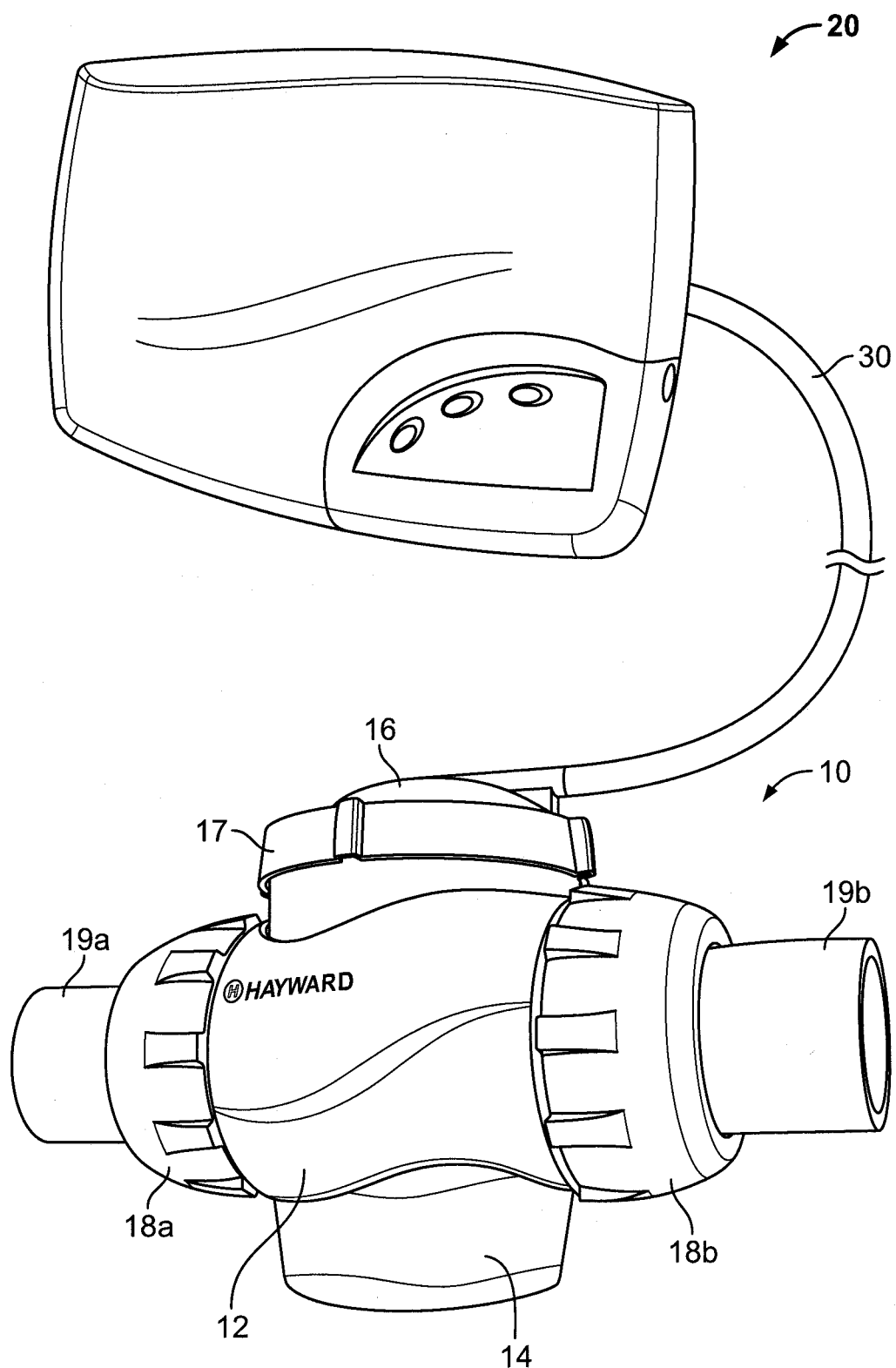
FIG. 1 is a perspective view of the controller and chlorinator of the present disclosure.

FIG. 1 is a perspective view of a controller 10 and a chlorinator 20 of the present disclosure, interconnected by a cable 30. The chlorinator 10 includes a casing 12, a transparent or translucent body 14, a screw cap 17, a first compression nut 18a, and a second compression nut 18b. The nuts 18a, 18b permit connection of a first pipe 19a and a second pipe 19b (such pipes forming part of the overall piping of a pool/spa equipment installation) to the chlorinator 10. The body 14 a houses a chlorinator cartridge (or cell, both terms being used interchangeably herein) 60 (see FIG. 5), discussed in greater detail below. The cable 30 extends from the controller 20 and connects to a cartridge lid 16 that couples to the chlorinator cartridge 60, both electrically and mechanically. The cable 30 extends from the exterior of the cartridge lid 16 to the interior, and by way of a plug, provides power and electrical communication between the controller 20 and the chlorinator cartridge 60. The cable 30 is sealed to the lid 16 so that no water (e.g., pool/spa water or rain water) can enter the chlorinator 10 and damage the internal circuitry. The cartridge lid 16 is sealingly secured to the chlorinator cartridge 60. The water-tight connection created by the screw cap 17 restricts any water from entering the chlorinator 10. It is noted that communication between the chlorinator 10 and the controller 20 could also be provided by way of a wireless connection in place of the cable 30.

Figure 2:
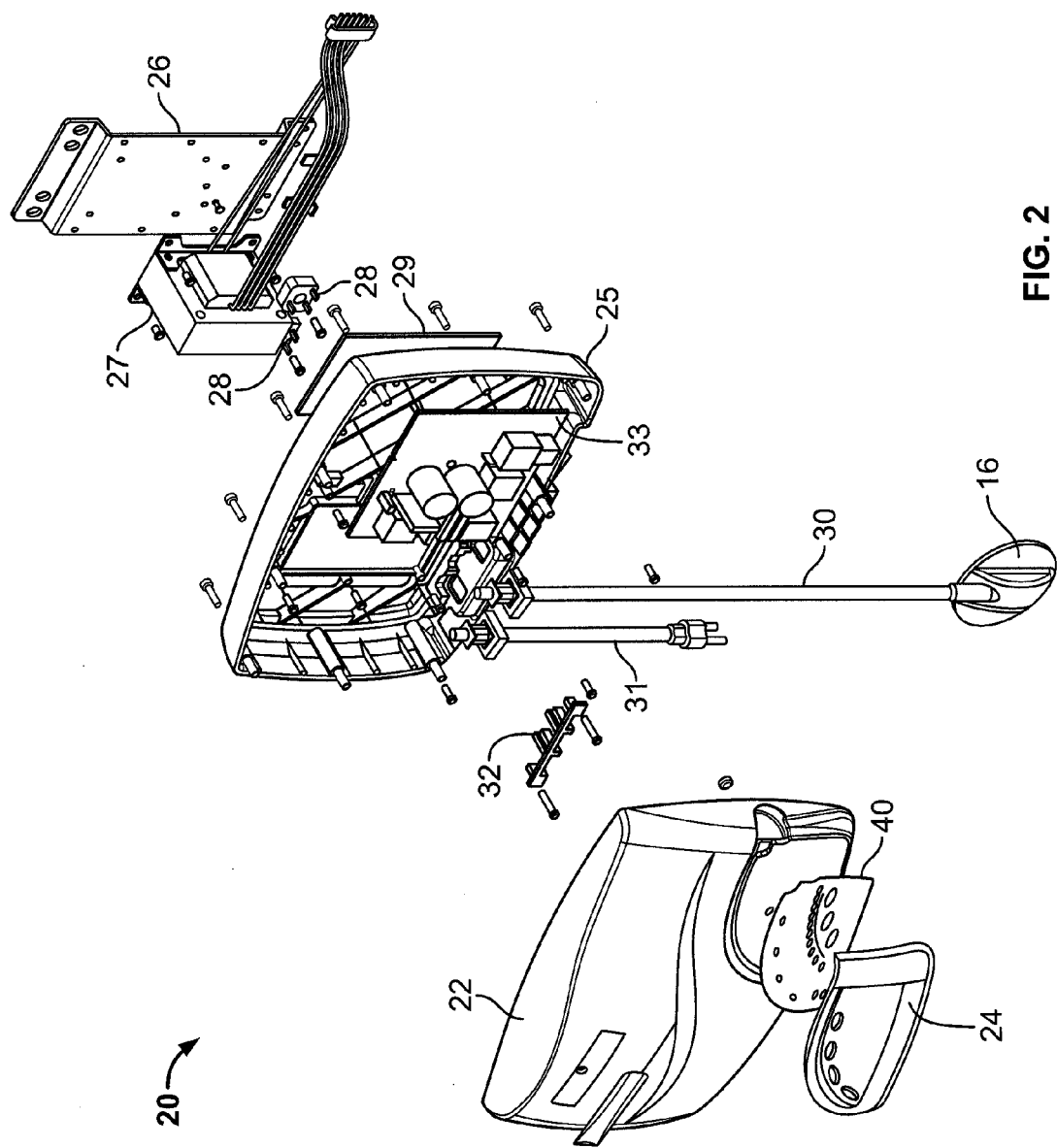
FIG. 2 is an exploded view of the controller of the present disclosure.

FIG. 2 is an exploded view of the controller 20. The controller 20 includes a front housing portion 22 having a movable cover 24, and a rear housing portion 25 attached to the front housing portion 22. An optional mounting plate 26 could be provided and attached to the rear housing portion 25 to allow mounting of the controller 20 to a surface (e.g., on a wall of a building, at a location near a pool/spa equipment pad, etc.). A transformer 27 provides electrical power to a printed circuit board 33 containing circuitry of the controller 20, as well as to the chlorinator 10. The transformer 27 steps incoming power at a household voltage level (e.g. 120 volts) to a lower voltage level for use by the controller 20 and the chlorinator 10. Two bridge rectifiers 28 convert alternating current (AC) provided by the transformer 27 to direct current (DC) for use by the controller 20 and chlorinator 10. The transformer 27, rectifiers 28, and printed circuit board 33 are housed by the housing portions 22 and 25. The housing portions 22 and 25 could be secured together by way of screws (as shown in FIG. 2), snap fit, fasteners, adhesive, etc. A power cord 31 (which can be plugged into a household AC outlet) provides power to the transformer 27. Both the cable 30 and the power cord 31 could be secured to the housing using a clamp 32 and associated fasteners. The cover 24 can be rotated downward (i.e., away from the housing portion 22) so as to provide access to a control panel 40. As discussed in greater detail below in connection with FIGS. 3-4, the control panel 40 includes lights (e.g., light-emitting diodes (LEDs) or incandescent lights) which indicate various operational, status, and diagnostic information relating to the chlorinator 10 and the cell 60, as well as buttons and/or a control knob for allowing a user to control operation of the chlorinator 10. It is noted that the housing portions 22, 25 could be made from plastic or other suitable material. A rear plate 29 is attached to the rear housing portion 25.

Figure 3:
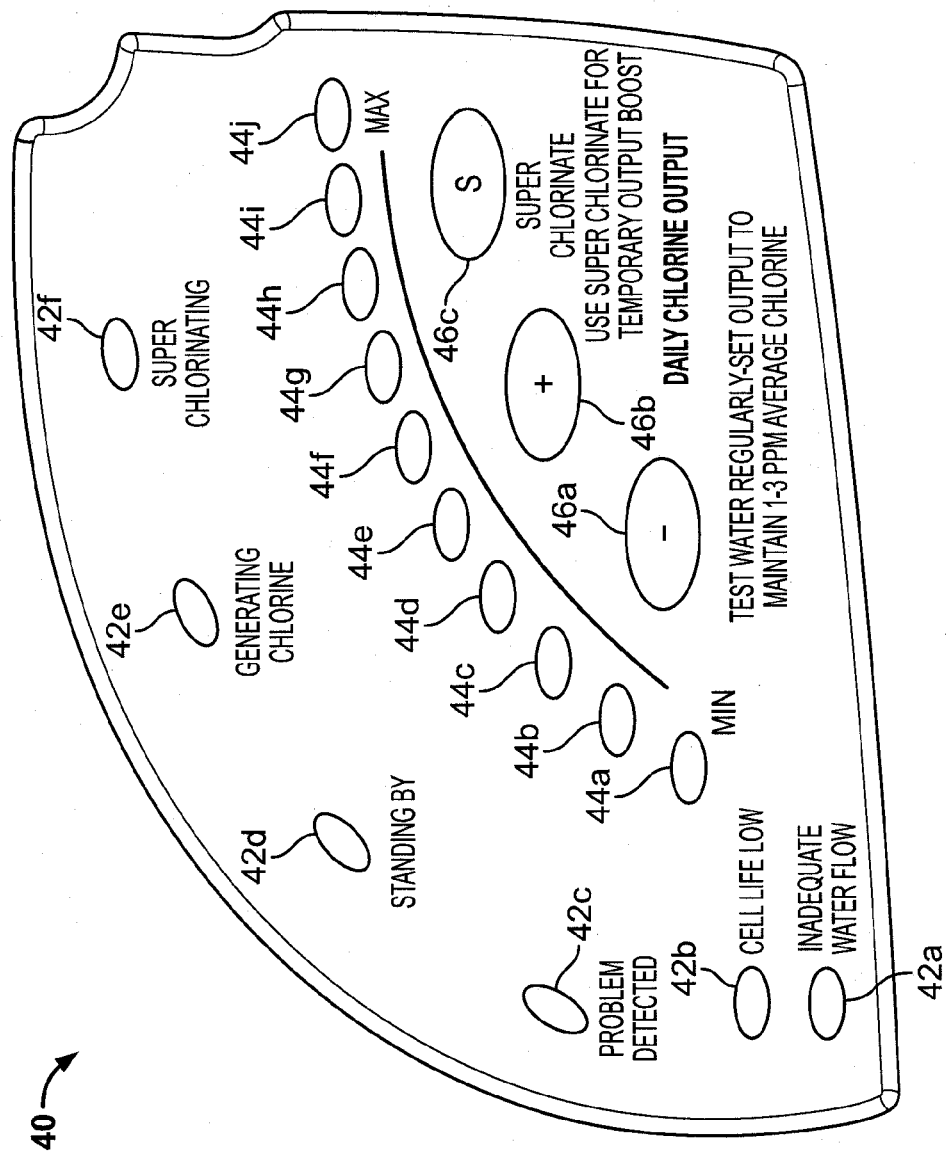
FIGS. 3-4 are partial front views of the controller of the present disclosure, showing the control panel of the controller in greater detail.

FIG. 3 is a diagram showing one embodiment of the control panel 40 of the controller 20. The panel 40 includes a plurality of status lights (e.g., LEDs) 42a-42f which indicate various conditions of the chlorinator 10, such as inadequate water flow through the chlorinator (light 42a), low cell life left (light 42b), a problem with the chlorinator and/or controller (light 42c), stand by state (light 42d), chlorine generation state (light 42e), and super chlorination state (light 42f). The plurality of status lights 42a-42f may alternatively be a single or a plurality of LCD screens or other display technology that is known. The inadequate water flow light 42a is illuminated when the controller 20 detects (via a flow sensor within the chlorinator 10) that inadequate or no water is flowing through the chlorinator 10. In such circumstances, the controller 20 halts operation of the chlorinator 10, thereby preventing damage to the chlorinator 10 and/or other components of a pool/spa system. The cell life low light 42b is illuminated when the controller 20 detects that the chlorinator cell 60 is approaching or is at the end of its useful life, thereby indicating that the cell should be replaced. The problem detected light 42c is illuminated when the controller 10 detects a malfunction/fault of the cell 60 and/or other components of the system. The standing by light 42d indicates that the chlorinator 10 is not operating but is in normal condition. The generating chlorine light 42e is illuminated by the controller 20 when the chlorinator 10 is generating chlorine. The super chlorinating light 42f is illuminated when the chlorinator is generating elevated levels of chlorine for a short period of time (e.g., to quickly boost the level of chlorine in a pool or spa). The panel 40 also includes a plurality of lights 44a-44j which indicate chlorine output levels. A plurality of membrane switches 46a-46c are provided for controlling the chlorine output level—by pressing the switch 46a, the user can decrease the level of chlorine generated by the chlorinator 10 (causing fewer of the lights 44a-44j to illuminate). Conversely, by pressing the switch 46b, the user can increase the level of chlorine generated by the chlorinator 10 (causing a greater number of the lights 44a-44j to illuminate). By pressing the switch 46c, the user can initiate super chlorination mode, which causes the chlorinator 10 to generate an increased level of chlorine for a pre-defined period of time (also causing the light 42f to illuminate during this time period). It is noted that the lights 42a-42f and 44a-44j could be different colors, and that they could flash to indicate different parameters or conditions to the user (e.g., a certain flashing sequence could be initiated to indicate a problem with a particular component).

Figure 4:
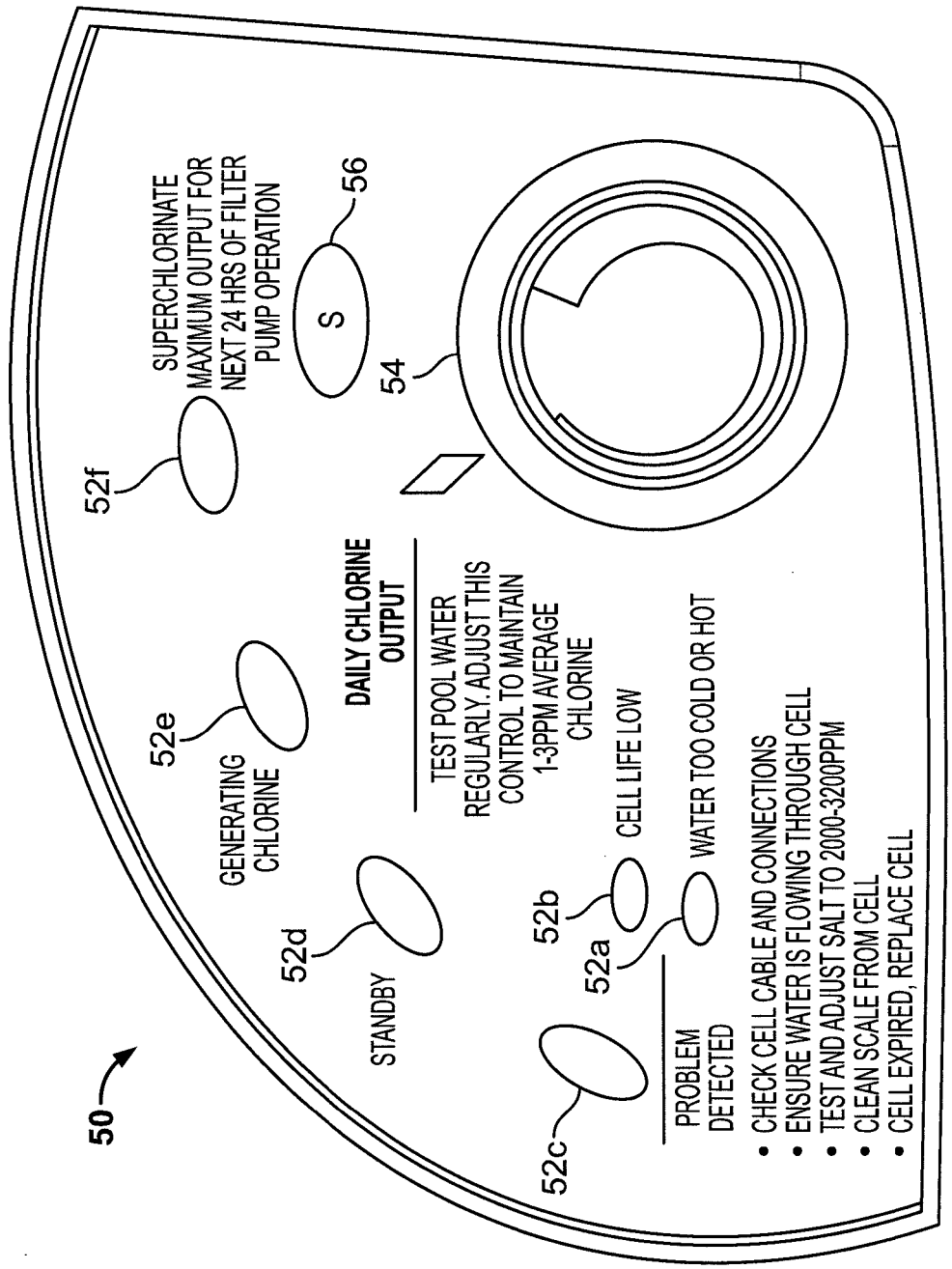

FIG. 4 is a partial front view of another embodiment of the control panel (indicated at 50) according to the present disclosure. In this embodiment, the control panel includes status lights (e.g., LEDs) 52a-52f as well as a control knob 54 and a button 56. The light 52a indicates whether sensed water temperature is too hot or too cold for chlorination. The light 52b indicates whether the usable remaining time (life) of the cell cartridge 60 is low. The light 52c indicates whether a problem has been detected with the cell cartridge 60 or another component. The light 52d indicates whether the system is in a standby condition (i.e., operating normally, but not currently generating chlorine). The light 52e indicates whether the chlorinator 10 is generating chlorine. The light 52f indicates whether the chlorinator 10 is in super chlorination mode. As with the embodiment shown in FIG. 3, the lights 52a-52f could be different colors, and could flash to indicate conditions/malfunctions to the user. The knob 54 can be rotated to increase or decrease chlorine output of the chlorinator 10. The button 56, when depressed, causes the chlorinator 10 to temporarily output an elevated level of chlorine (super chlorination).

Figure 5:
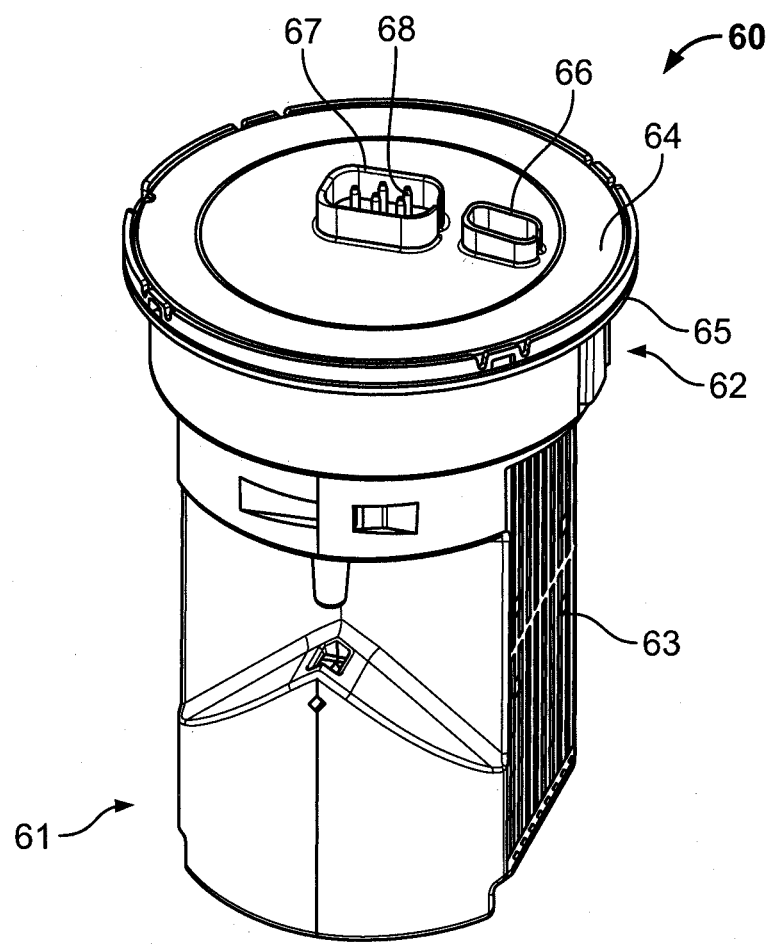
FIG. 5 is perspective view of the replaceable cell cartridge of the present disclosure.

FIG. 5 is perspective view of the replaceable cell cartridge 60 of the present disclosure. The cartridge 60 can be installed by a user into the chlorinator 10, and replaced as necessary. The cartridge 60 includes a cartridge body 61, a cartridge cap 62, a plurality of slots 63 aligned with a plurality of electrically-charged plates (blades) positioned within the cartridge 60, a cover 64 and an o-ring 65. The cover 64 includes a locking key 66 and an electrical connector 67 having a plurality of connector pins 68. The electrical connector 67 is shaped so that it is compatible with the shape of a plug (not shown) formed in the cap 16, so that only compatible cartridges can be used with the chlorinator 10. The plurality of connector pins 68 extend through the cover 64 and are in electrical connection with the electrical components of the cartridge 60. As discussed in greater detail below in connection with FIG. 7, the cartridge 60 includes an on-board processor and associated non-volatile memory for storing parameters relating to the cartridge 60, as well as sensors for sensing various conditions relating to water being chlorinated. The on-board processor also includes firmware for authenticating the cartridge 60 with the controller 10, so that only authorized cartridges are operable with the controller 10. When the cartridge 60 is inserted into the chlorinator 10, the o-ring 65 creates a seal between the cartridge 60 and the chlorinator 10 so that no water escapes from the chlorinator 10. The o-ring 65 may alternatively be a flat gasket or other sealing agent, or replaced by any other known sealing methodology. The cartridge 60 can be removed from the chlorinator 10 as necessary by a user and replaced.

Figure 6:
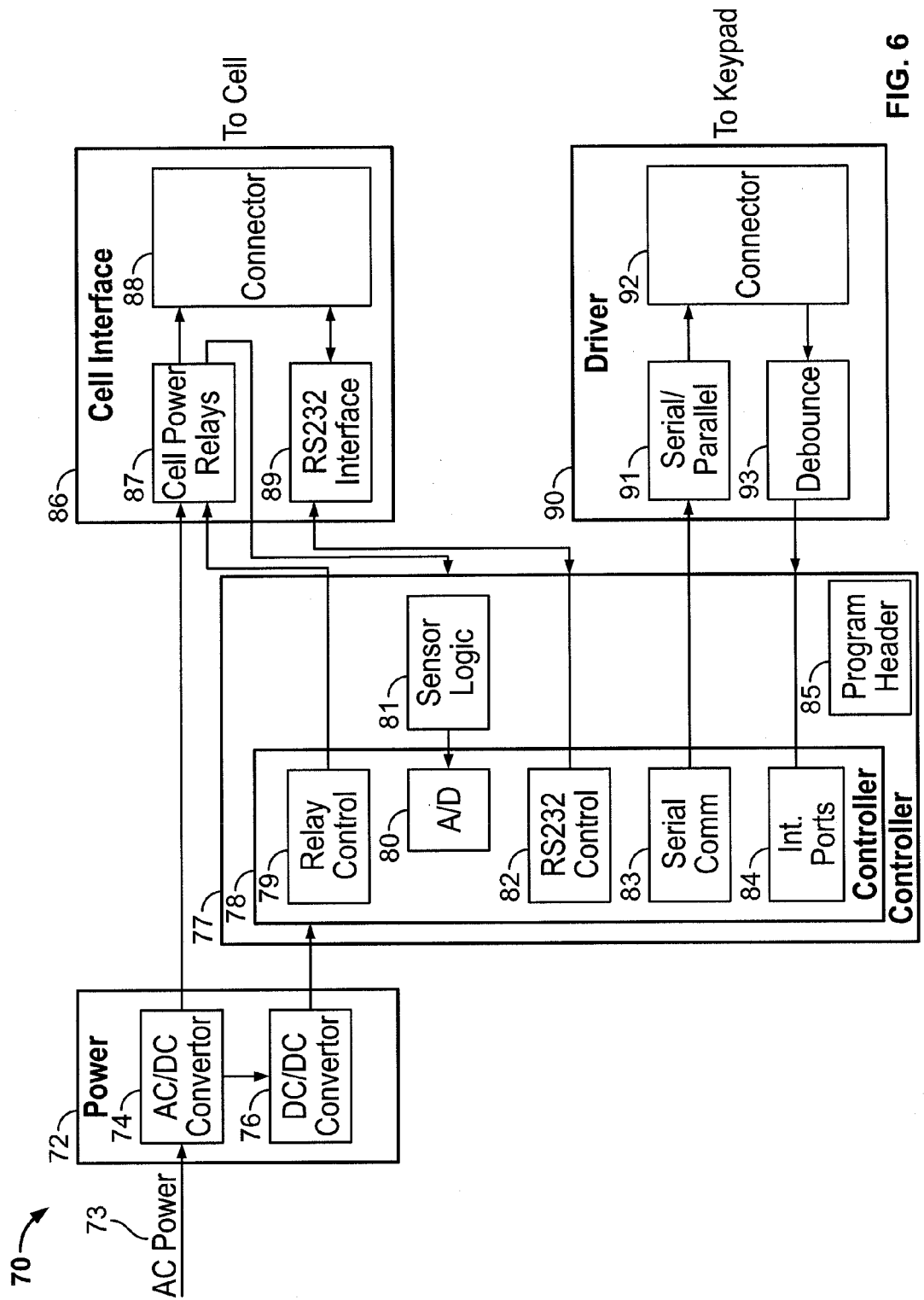
FIG. 6 is a schematic diagram illustrating electrical and software components of the controller of the present disclosure.

FIG. 6 is a schematic diagram, indicated generally at 70, illustrating electrical and software components of the controller 20 of the present disclosure. The controller 20 includes a power supply 72, a controller subsystem 77, a cell (cartridge) interface 86, and driver subsystem 90. The power supply 72 provides power to the controller subsystem 77, the cell interface 86, and the driver subsystem 90, as well as power to the chlorinator 10. The power supply 72 includes an alternating current (AC) to direct current (DC) converter 74 which coverts household AC power 73 (supplied by the power cable 31 shown in FIG. 2) to DC power, and a DC to DC converter 76 which converts DC output of the converter 74 to direct current of a different voltage level for subsequent use by the control subsystem 77.

The control subsystem 77 includes a controller integrated circuit (IC) 78 having a number of functional components including relay control logic 79, an analog-to-digital (A/D) converter 80, a serial (RS-232) communications controller 82, a serial communications module 83, and interrupt ports 84. The controller IC 78 could be the PIC16F1938 microcontroller manufactured by MICROCHIP, INC., or any other suitable equivalent. The control subsystem 77 also includes non-volatile, computer-readable memory which stores the control processes disclosed herein in the form of computer-readable instructions capable of being executed by the controller IC 78. Such instructions could be accessed from the memory by way of a software program header 85. The memory could be separate from the controller IC 78 (i.e., on another IC chip) or it could be provided on the controller IC 78. The control subsystem 77 also includes sensor logic 81 for determining the state of one or more power relays of the cell interface 86.

The driver subsystem 90 permits communication between the buttons of the control panel (keypad) 40 or 50, and includes a serial-to-parallel converter 91, a debounce circuit 93, and a connector 92 for connection with the control panel 40 or 50. The driver 90 receives control commands entered by a user at the control panel 40 or 50, processes same, and transmits the commands to the controller subsystem 77 for execution thereby. The control subsystem 77 also controls the various status lights of the control panel 40 or 50.

The cell interface 86 includes cell power relays 87, a connector 88, and a communications (RS-232) interface 89. The cell power relays 87 selectively control power delivered to the cell (cartridge) 60 of the chlorinator 10, and are controlled by the relay control logic 79 of the controller IC 78. The communications interface 89 permits bidirectional serial data communications between the controller subsystem 77 and the on-board processor of the cartridge 60. The connector 88 mates with the port 67 and has a shape that matches the port 67.

Figure 7:
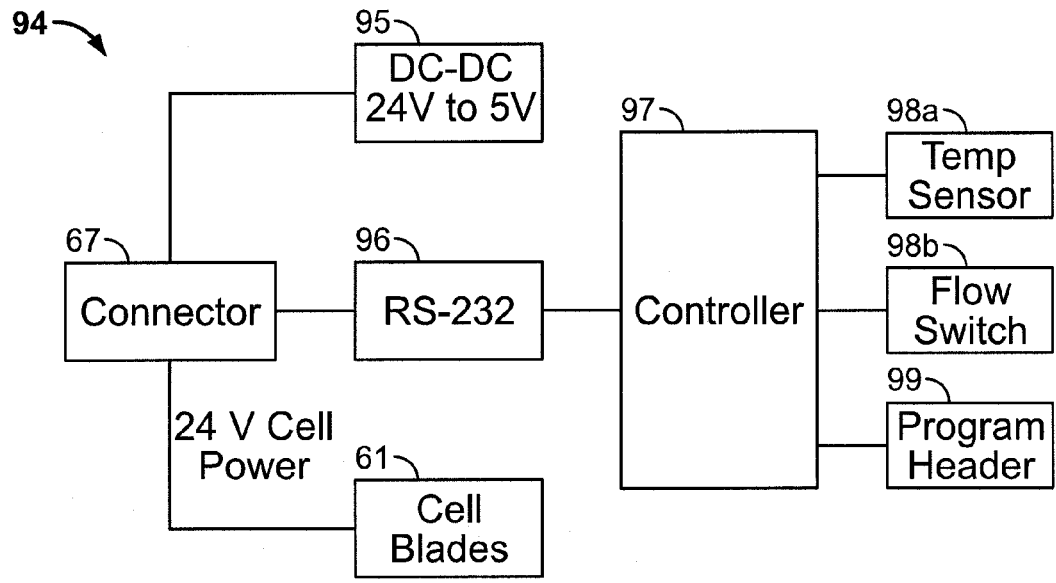
FIG. 7 is a schematic diagram illustrating electrical and software components of the cell cartridge of the present disclosure.

FIG. 7 is a schematic diagram, indicated generally at 94, illustrating electrical and software components of the cell (cartridge) 60 of the present disclosure. The connector 67 is in electrical communication with a DC-to-DC converter 95 which, for example, converts 24 volts DC current supplied to the cartridge 60 by the controller 20 to a lower voltage level of 5 volts. A communications transceiver (RS-232) 96 is provided in the cartridge 60 and permits bidirectional serial data communications between the cartridge 60 and the controller 20. The cartridge 60 also includes a controller IC 97 in communication with one or more sensors such as a temperature sensor 98a for measuring water temperature and/or a flow switch 98b for sensing water flow. The controller 97 obtains sensed parameters from the sensors 98a, 98b and, upon receiving a request from the controller 20, transmits the sensed parameters to the controller 20 using the communications transceiver 96. A non-volatile memory 100 (see FIG. 8) associated with, or forming part of, the controller IC 97 stores parameters associated with the cartridge 60 as well as an authentication/encryption key that can be used to authenticate the cartridge 60 with the controller 20 and/or allow for encrypted communications therebetween. Advantageously, authentication permits operation of only authorized cartridges with the controller 20. Control/program logic executed by the cartridge 60, in the form of computer-readable instructions, could be stored in the on-board non-volatile memory 100, and could be accessed by the controller IC 97 by way of a software program header 99. It is noted that other sensors could be provided on-board the cartridge 60, such as a pH sensor, an ORP sensor, and/or other sensors, and the controller IC 97 could be configured to obtain sensed levels from such sensors and transmit same to the controller 20. The on-board controller IC 97 could be the PIC16F1823 microcontroller manufactured by MICROCHIP, INC., or any other suitable equivalent.

Figure 8:
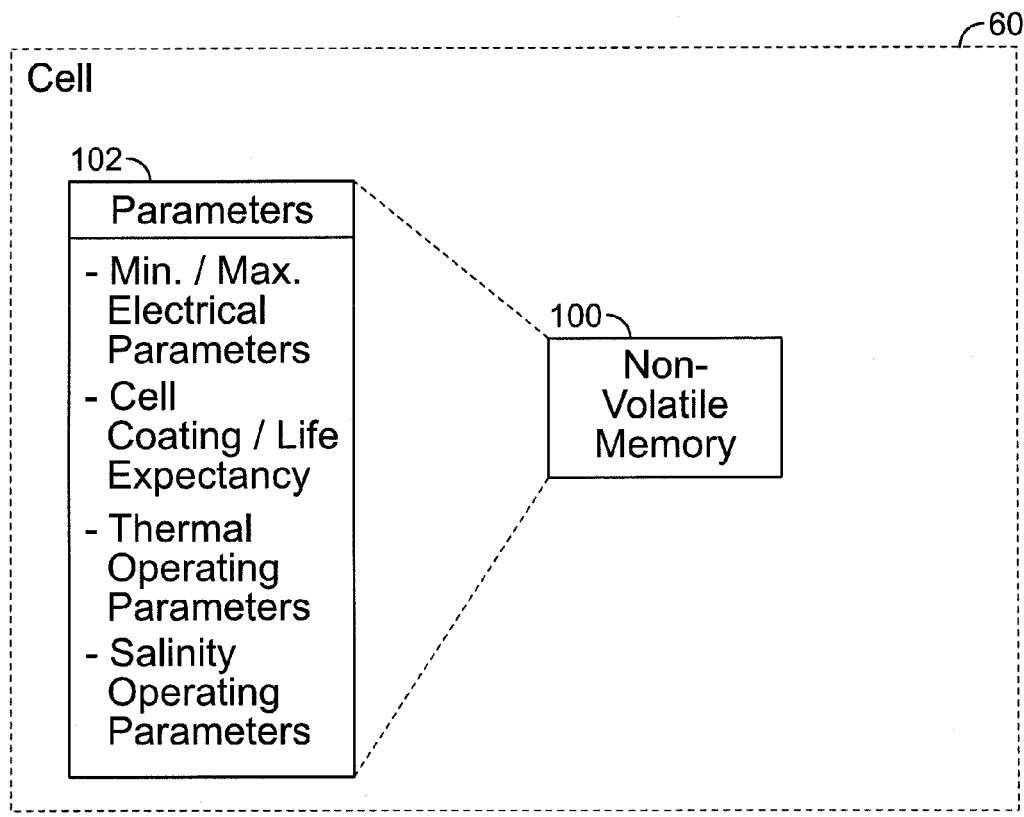
FIG. 8 is a diagram illustrating non-volatile memory of the cell cartridge of the present disclosure, and sample parameters capable of being stored in the non-volatile memory.

FIG. 8 is a diagram illustrating non-volatile memory 100 of the cell cartridge 60 of the present disclosure, and sample parameters 102 capable of being stored in the non-volatile memory 100. Parameters 102 which could be stored in the non-volatile memory 100 include, but are not limited to, minimum/maximum electrical parameters associated with the cartridge 60, cell coating and/or life expectancy (i.e., information relating to materials used to coat the plates/blades of the cell, as well as total expected operational lifetime of the cell), thermal operating parameters, salinity operating parameters, etc. The parameters 102 could be loaded into the memory 100 by a manufacturer of the cartridge 60, and/or they could be updated during use of the cartridge 60 (e.g., by the controller 20).

Figure 9:
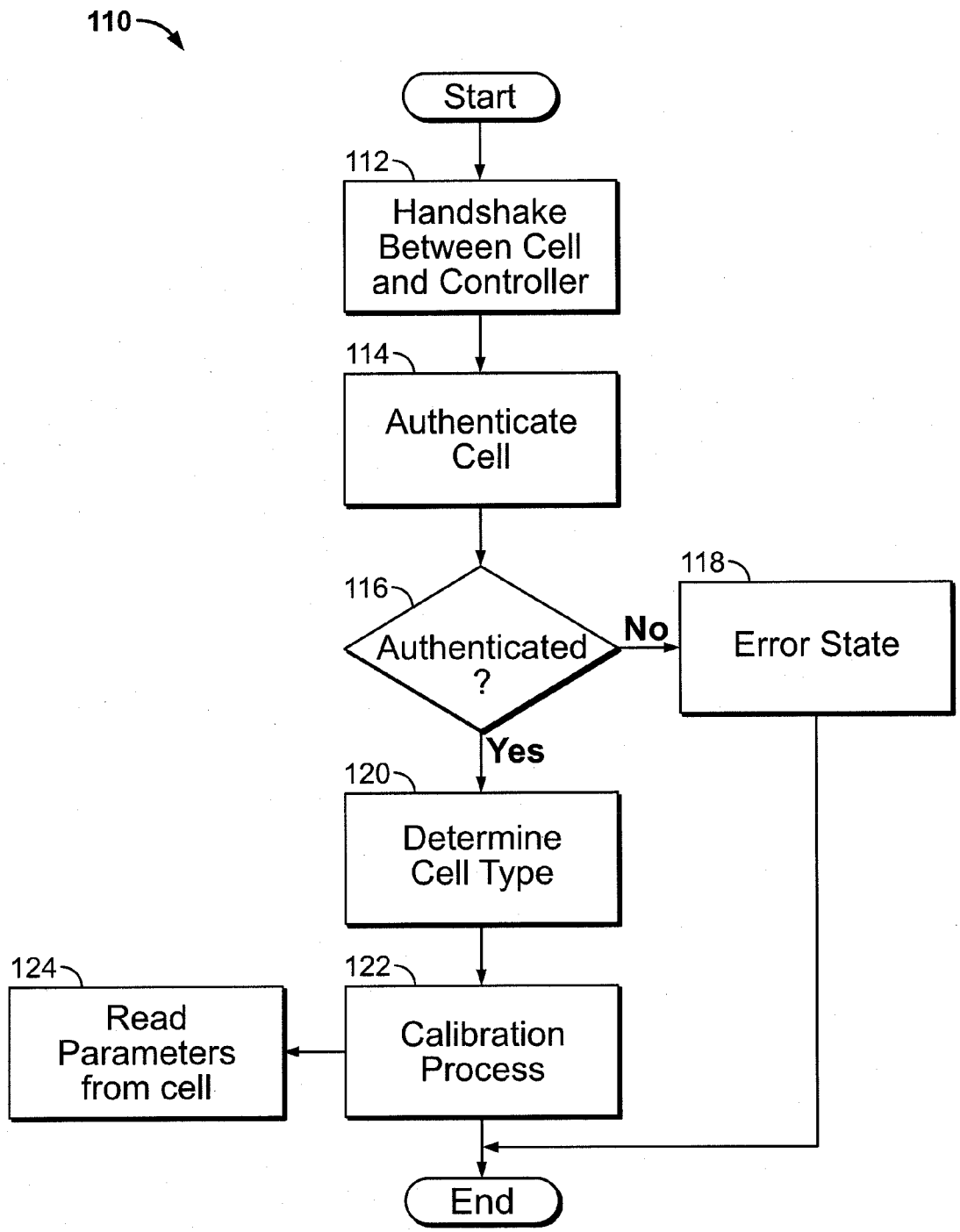
FIG. 9 is flowchart showing processing steps according to the present disclosure for communication with the cell cartridge by the controller, as well as authentication of the cell cartridge and calibration of the cell.

FIG. 9 is flowchart showing processing steps according to the present disclosure, indicated generally at 110, for communication with the cell cartridge 60 by the controller 20, as well as authentication of the cell cartridge 60 and calibration of the cell 60. Beginning in step 112, a communications "handshake" is exchanged between the cell 60 and the controller 20, to establish a communications link between the two components. In step 114, the cell 60 transmits an authentication key to the controller 20. Any suitable authentication technique could be used, such as the AES encryption standard or any other suitable equivalent. The transmitted authentication key is processed by the controller 20, and a determination is made in step 116 as to whether the cell 60 is authenticated. If not, step 118 occurs, wherein the controller 20 enters an error state and operation of the cell 60 is not permitted. Otherwise, if the cell 60 is authenticated, step 120 occurs, wherein the controller 20 determines the type of the cell 60. For example, by communicating with the cell 60, the controller could determine whether the cell 60 is an extended-life cell or a cell having a reduced lifetime. In step 122, once the cell type has been determined, the controller 20 executes a calibration process for calibrating operation of the cell 60. To do so, in step 124, the controller 20 reads one or more parameters from the cell 60. It is noted that the cell 60 could be authenticated upon the first communication between the controller 20 and the cell 60 after system power-up, periodically, or every time a communication occurs between the controller 20 and the cell 60.

Figure 10:
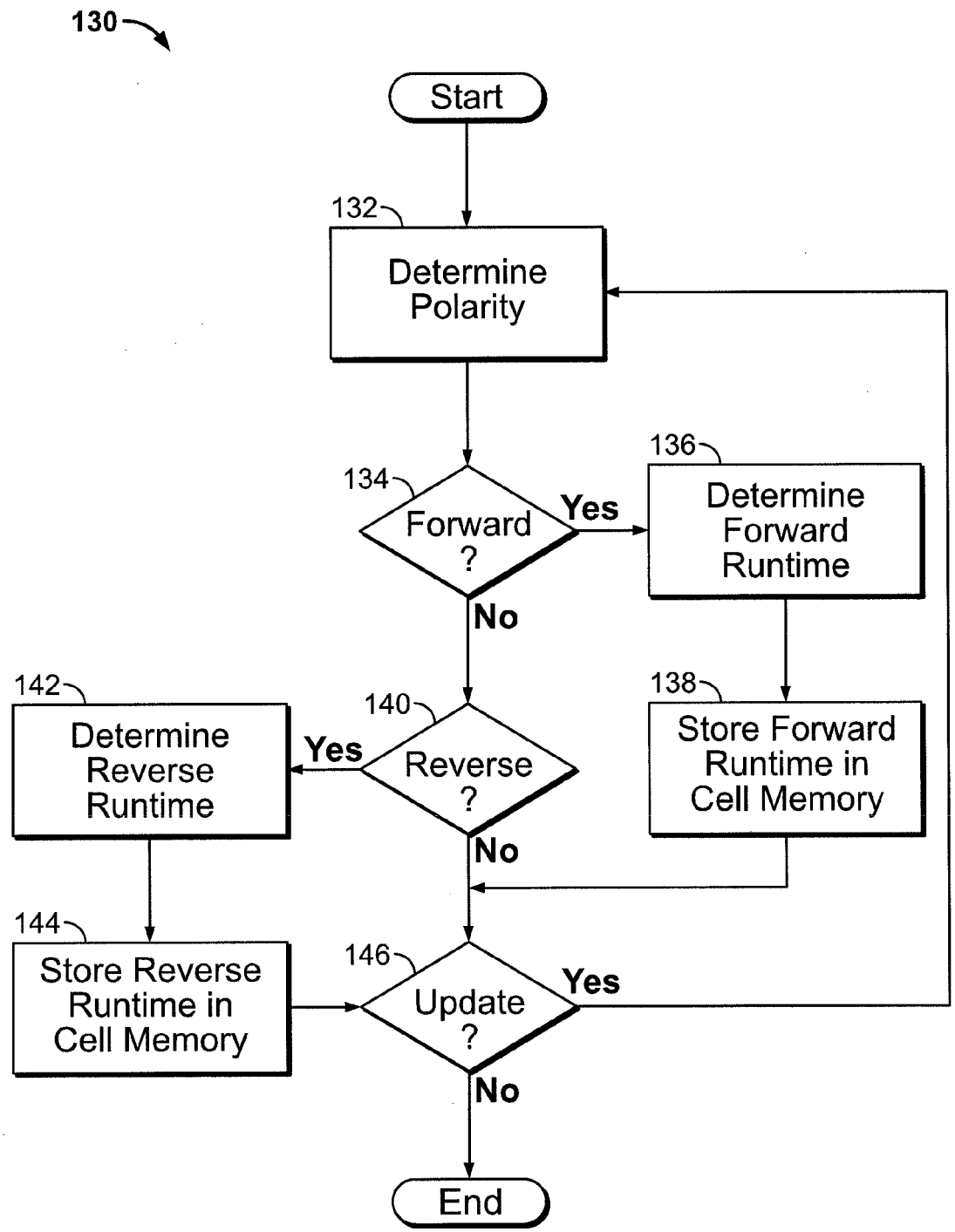
FIG. 10 is a flowchart showing processing steps according to the present disclosure for storing information in non-volatile memory of the cell cartridge relating to run times.

FIG. 10 is a flowchart showing processing steps, indicated generally at 130, according to the present disclosure for storing information in non-volatile memory 100 of the cell cartridge 60 relating to run times, i.e., the amount of time that the cell 60 has been operated. In step 132, the controller IC 97 of the cell 60 determines the polarity being applied to the cell 60. In step 134, a determination is made as to whether the polarity applied to the cell 60 is forward polarity. If so, steps 136 and 138 occur, wherein the controller IC 97 determines the forward run time and stores the forward run time in the non-volatile memory 100 of the cell 60. Otherwise, step 140 occurs, wherein the controller 97 determines whether the polarity applied to the cell 60 is reverse polarity. If so, steps 142 and 144 occur, wherein the controller IC 97 determines the reverse run time and stores the reverse run time in the non-volatile memory 100 of the cell 60. In step 146, a determination is made as to whether to update the run time information for the cell 60. If so, control returns to step 132; otherwise, processing ends. By storing forward and reverse run time information in the non-volatile memory 100 of the cell 60, it is possible to track the total amount of time that the cell 60 has been in operation (i.e., by adding the forward and reverse run times), as well as the number of times polarity has been reversed. This information is useful for identifying the total amount of life left in the cell 60, as well as for other diagnostic purposes.

Figure 11:
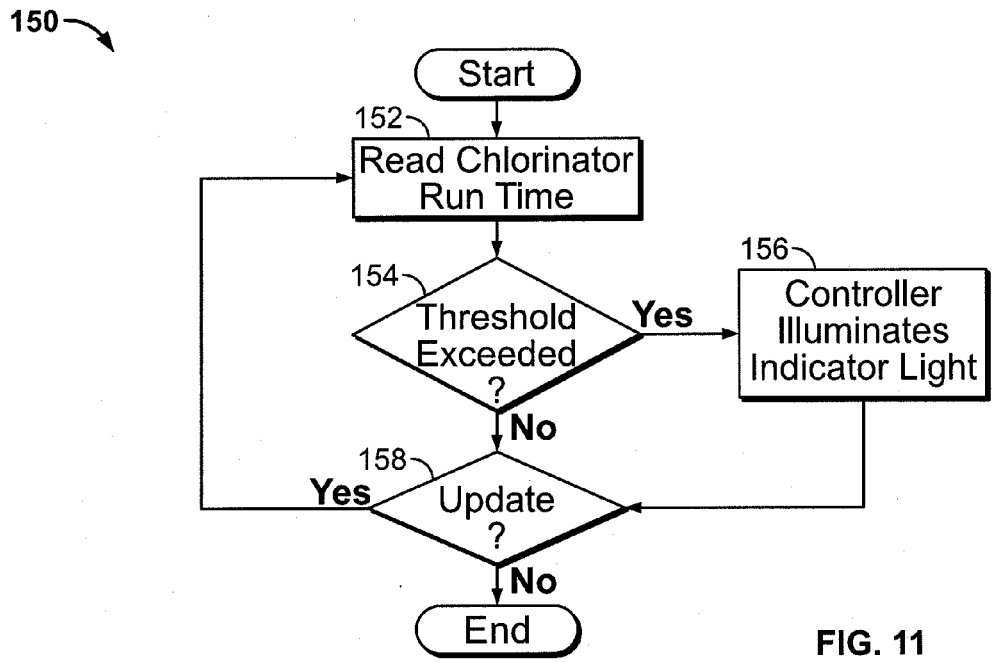
FIG. 11 is a flowchart showing processing steps according to the present disclosure for reading run time information from non-volatile memory of the cell cartridge, determining whether the run time exceeds a threshold, and indicating same to a user.

FIG. 11 is a flowchart showing processing steps according to the present disclosure, indicated generally at 150, for reading run time information from non-volatile memory 100 of the cell cartridge 60, determining whether the run time exceeds a threshold, and indicating same to a user. In step 152, run times (both forward and reverse run time) are read from the non-volatile memory 100 of the cell 60, and total run time is calculated. Then, in step 154, a determination is made as to whether the total run time exceeds a pre-defined threshold. If so, step 156 occurs, wherein the controller 20 illuminates an indicator light on the panel 40, i.e., the cell life low lights 42b or 52d shown in FIGS. 3-4. The illuminated light indicates to the user that the cell 60 should be replaced with a new cell. Otherwise, step 158 occurs, wherein a determination is made as to whether to update the run time information. If so, control returns to step 152; otherwise, processing ends.

Figure 12:
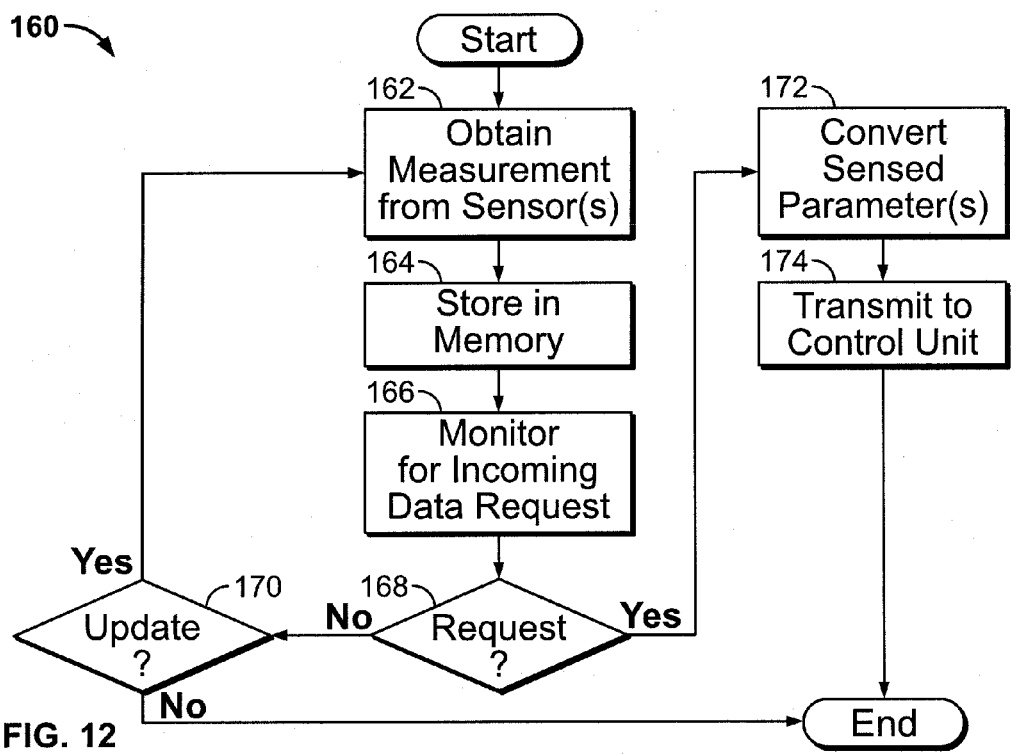
FIG. 12 is a flowchart showing processing steps according to the present disclosure for storing sensed information in memory of the cell cartridge and transmitting such information to the controller.

FIG. 12 is a flowchart showing processing steps according to the present disclosure, indicated generally at 160, for storing sensed information in memory 100 of the cell cartridge 60 and transmitting such information to the controller 20. In step 162, the controller IC 97 of the cell 60 obtains measurements from one or more of the sensors 98a, 98b, including, but not limited to, temperature, flow rate, pH, ORP, etc. Then, in step 164, the controller IC 97 stores the obtained measurements in the non-volatile memory 100. In step 166, the controller IC 97 monitors for an incoming request for data, i.e., a request generated by the controller 20 and transmitted to the cell 60. Then, in step 168, a determination is made as to whether a request has been received. If so, steps 172 and 174 occur, wherein the sensed measurements (parameters) stored in the non-volatile memory 100 are converted into communications protocol format and the converted information is transmitted from the cell 60 to the control unit 20 via the cable 30 or wirelessly. Otherwise, step 170 occurs, wherein a determination is made as to whether to update the measurements/parameters. If so, control returns back to step 162; otherwise, processing ends. It is noted that a wide variety of measurements/parameters could be obtained and stored in non-volatile memory 100 of the cell 60, including, but not limited to, chlorine parts per million (ppm), ORP, pH, salt ppm, turbidity, calcium hardness, and other parameters, and such parameters could be transmitted to the controller 20 for processing thereby.

Figure 13:
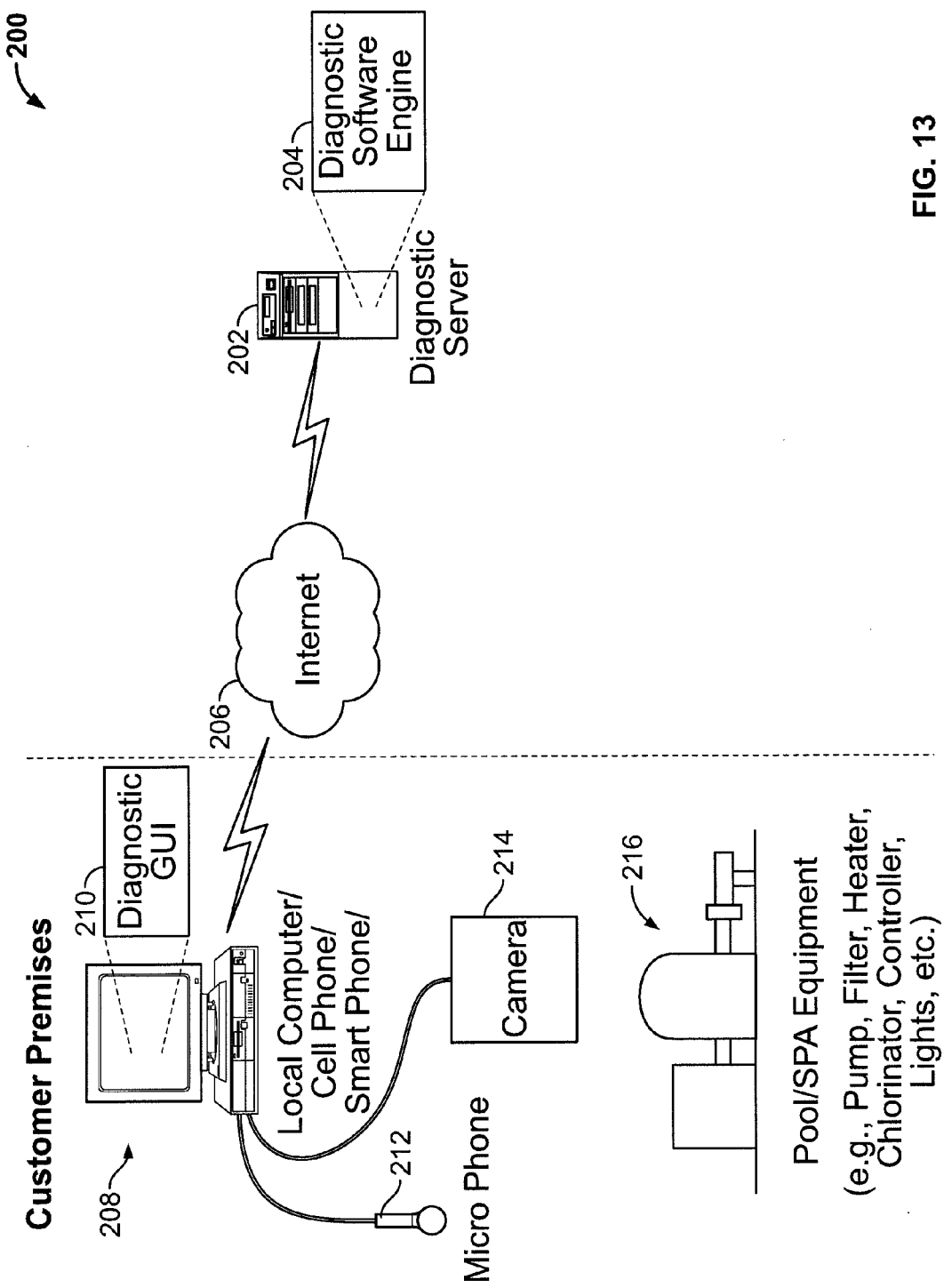
FIG. 13 is a diagram illustrating a system according to the present disclosure for remotely diagnosing errors and/or malfunctions associated with pool/spa equipment.

FIG. 13 is a diagram illustrating a system according to the present disclosure, indicated generally at 200, for remotely diagnosing errors and/or malfunctions associated with pool/spa equipment. The system 200 includes a diagnostic server 202 which executes a diagnostic software engine 204, in communication with a local application executing on a computer system 208. Communication could be by way of the Internet 206, a local area network (LAN), a wide area network (WAN), a cellular network, etc. The computer system 208 could be a personal computer, tablet computer, cellular phone, smart phone, etc., and the local application executed by the computer system 208 generates a diagnostic graphical user interface (GUI) display 210 that is displayed on a display of the computer system 208. The GUI 210 could replicate one or more control panels of the pool/spa equipment 216, e.g., the GUI 210 could appear identical to the control panels 40 or 50 shown in FIGS. 3-4. When a malfunction of the equipment 216 occurs, the user can replicate the appearance of indicator lights appearing on the control panel(s) of the equipment 216 using the GUI 210. For example, if the control panel 40 has three lights flashing intermittently, by using a mouse and clicking on the replicated control panel appearing on the GUI 210, the user can replicate the same three flashing lights on the GUI 210. Once the replicated control panel condition is created in the GUI 210, the local application transmits same to the diagnostic server 202, for processing by the diagnostic software engine 204. Based upon the replicated conditions generated in the GUI 210, the diagnostic software engine 204 formulates a solution to the problem, and transmits the solution to the local computer 208 for subsequent display to the user. An explanation of the error condition could also be provided to the user. Of course, the functionality provided by diagnostic software engine 204 could be provided within the local computer system 208, such that communication with the diagnostic server 202 is not necessary.

It is noted that the local computer system 208 could also include a microphone 212 and a camera 214, both or either of which could be used to obtain information about the malfunctioning equipment 216. Thus, for example, if a pump is making a high-pitched whining noise, the user could record the sound using the microphone 212 and transmit the recorded sound to the diagnostic server 202 using the local application, whereupon the recorded sound is processed by the software engine 204 (e.g., the recorded sound is compared to a database of sounds made by pumps which are indicative of various conditions) and a solution to the problem is generated and transmitted back to the local computer system 208 for display to the user. Also, for example, a picture of the current operating conditions of the equipment 216 could be taken using the camera 214, and transmitted to the diagnostic server 202. Using image processing, the software engine 204 could analyze the picture to determine the error condition, and a solution could be generated and transmitted to the local computer system 208 for display to the user.

It is noted that an entirely local solution could be provided such that the server 202 is not needed. In such circumstances, the functionality of the diagnostic software engine 204 could be provided within the application executing on the local computer system 208. Moreover, the GUI 210 could include a three-dimensional model of the user's pool/spa, and the user could re-create the present configuration of the pool/spa and condition of associated equipment using the model. For example, the user can "drag-and-drop" representations of items such as a pool skimmer, main drain, lights, stairs, and other pool features into the model. Once the model is created, an algorithm (executing locally on the local computer system 208, or remotely on the diagnostic server 202) can analyze the model and recommend a specific manner in which to operate pool/spa equipment in order to obtain better results (e.g., it could recommend better ways of operating a pool/spa cleaner (or of programming same) based upon the model created by the user). Further, the algorithm could produce a new cleaning program based upon the model, which could be downloaded to a robotic pool cleaner (e.g., via USB, wirelessly, etc.).

Although the foregoing disclosure was discussed in connection with pools and spas, it is to be understood that the systems and methods disclosed herein could be utilized in connection with any body of water where sanitization is necessary, e.g., fountains, ponds, water features, etc.

Having thus described the invention in detail, it is to be understood that the foregoing description is not intended to limit the spirit or scope thereof. What is desired to be protected is set forth in the following claims.

What is claimed is:

1. A system for controlling a chlorinator, comprising:
a chlorinator including a body and a replaceable chlorinator cartridge removably positionable within said body, said chlorinator cartridge including a cartridge body, a cartridge cap having a connector, a plurality of electrolytic plates within the cartridge body, a memory, and a processor in electrical communication with the plurality of plates and the memory of the cartridge;
a controller in electrical communication with said chlorinator, said controller including a control panel for allowing a user to control operation of said chlorinator,
wherein said processor of said chlorinator cartridge communicates with said controller to authenticate said chlorinator cartridge, said controller prohibiting operation of said chlorinator cartridge if said chlorinator cartridge is not authenticated;
wherein said cartridge houses said memory, said processor, and said plates; and
wherein said cartridge, said memory, said processor and said plates form a single unit removable from the chlorinator.

2. The system of claim 1, wherein said memory stores an authentication key, said processor transmitting said authentication key to said controller for subsequent authentication of said chlorinator cartridge.

3. The system of claim 2, wherein said memory stores one or more parameters relating to said chlorinator cartridge.

4. The system of claim 3, wherein said one or more parameters comprises one or more of a minimum electrical parameter associated with said chlorinator cartridge, a maximum electrical parameter associated with said chlorinator cartridge, a cell coating condition, a life expectancy associated with said chlorinator cartridge, a thermal operating parameter associated with operation of the chlorinator cartridge, a running time associated with said chlorinator cartridge, or a salinity operating parameter.

5. The system of claim 4, wherein said processor transmits said one or more parameters to said controller for subsequent processing by said controller.

6. The system of claim 1, wherein said control panel further comprises means for indicating operational, status, or diagnostic information relating to the chlorinator.

7. The system of claim 6, wherein said control panel further comprises a control knob for controlling chlorination output of the chlorinator.

8. The system of claim 7, wherein said control panel further comprises a plurality of switches for controlling operation of the chlorinator.

9. The system of claim 1, wherein said controller further comprises a movable cover for covering the control panel.

10. The system of claim 1, wherein the control panel is mountable at a location remote from said chlorinator.

11. The system of claim 1, wherein said chlorinator cartridge further comprises at least one sensor for sensing a condition relating to water being chlorinated by the chlorinator.

12. The system of claim 1, wherein said chlorinator cartridge further comprises a shaped electrical connector for electrical connection to a cable interconnecting said chlorinator with said controller.

13. A method for controlling a chlorinator, comprising the steps of:
    establishing a communications link between a chlorinator and a controller, the chlorinator including a body and a replaceable chlorinator cartridge removably positionable within said body, said chlorinator cartridge including a cartridge body, a cartridge cap having a connector, a plurality of electrolytic plates within the cartridge body, a memory, and a processor in electrical communication with the plurality of plates and the memory of the cartridge, wherein said cartridge houses said memory, said processor, and said plates; wherein said cartridge, said memory, said processor and said plates form a single unit removable from the chlorinator;
    retrieving an authentication key from the memory of the chlorinator cartridge removably positioned within said chlorinator;
    transmitting the authentication key from said chlorinator to said controller;
    processing the authentication key at the controller to determine whether the chlorinator cartridge is authenticated; and
    operating the chlorinator using the controller if the cartridge is authenticated by the controller.

14. The method of claim 13, further comprising prohibiting operation of the chlorinator if the cartridge is not authenticated by the controller.

15. The method of claim 13, further comprising accessing one or more parameters stored in said memory of said chlorinator cartridge using said controller.

16. The method of claim 15, further comprising adjusting operation of said chlorinator or said controller based upon said one or more parameters.

17. The method of claim 13, further comprising reading run time information from said memory of said chlorination cartridge using said controller and determining whether said run time exceeds a threshold.

18. The method of claim 17, further comprising indicating to a user who is using the controller that said chlorination cartridge should be replaced if said run time exceeds said threshold.

19. A chlorinator comprising:
    a chlorinator body including a first flow port and a second flow port on opposite sides of the chlorinator body and being coaxially aligned such that the first flow port and the second flow port share a first axis extending through centers of the first flow port and the second flow port; and
    a replaceable chlorinator cartridge removably positionable within said chlorinator body along a second axis transverse to the first axis,
    said chlorinator cartridge including a plurality of electrolytic plates and at least one circuit element in electrical communication with said plurality of plates,
    said replaceable cartridge housing said plurality of plates and said at least one circuit element,
    said cartridge, said plurality of plates and said at least one circuit element forming a single unit removable from said chlorinator body, and
    said plurality of plates of said chlorinator cartridge positioned along said first axis such that water flows along said first axis extending through said first flow port, through said plurality of plates housed in said chlorinator cartridge, and out of the second flow port.

20. The chlorinator of claim 19, wherein said chlorinator cartridge further comprises a memory for storing an authentication key, a processor transmitting said authentication key to a controller for subsequent authentication of said chlorinator cartridge.

21. The chlorinator of claim 20, wherein said memory stores one or more parameters relating to said chlorinator cartridge.

22. The chlorinator of claim 21, wherein said one or more parameters comprises one or more of a minimum electrical parameter associated with said chlorinator cartridge, a maximum electrical parameter associated with said chlorinator cartridge, a cell coating condition, a life expectancy associated with said chlorinator cartridge, a thermal operating parameter associated with operation of the chlorinator cartridge, a running time associated with said chlorinator cartridge, or a salinity operating parameter.

23. The chlorinator of claim 22, wherein said processor transmits said one or more parameters to said controller for subsequent processing by said controller.

24. The chlorinator of claim 19, wherein said chlorinator cartridge further comprises at least one sensor for sensing a condition relating to water being chlorinated by the chlorinator.

25. The chlorinator of claim 19, wherein said chlorinator cartridge further comprises a shaped electrical connector for electrical connection to a cable interconnecting said chlorinator with said controller.

* * * * *

UNITED STATES PATENT AND TRADEMARK OFFICE
CERTIFICATE OF CORRECTION

PATENT NO. : 9,885,193 B2
APPLICATION NO. : 13/562128
DATED : February 6, 2018
INVENTOR(S) : Chen et al.

It is certified that error appears in the above-identified patent and that said Letters Patent is hereby corrected as shown below:

On the Title Page

On Page 3, item [56], References Cited, Other Publications, "Extended European Search Report dated Oct. 26, 2015..." should read --Partial Supplementary European Search Report dated Oct. 26, 2015...--

In the Drawings

On Sheet 7, FIG. 7, reference numeral "61" should read --63--

In the Specification

Column 3, Lines 50-51, "a controller 10 and a chlorinator 20" should read --a controller 20 and a chlorinator 10--

Column 3, Line 58, "body 14 a houses" should read --body 14 houses--

Column 4, Line 65, "controller 10" should read --controller 20--

Column 5, Line 56, "cap 16" should read --lid 16--

Column 5, Line 67, "controller 10" should read --controller 20--

Column 6, Line 1, "controller 10" should read --controller 20--

Column 8, Line 40, "lights 42b or 52d" should read --lights 42b or 52b--

In the Claims

Claim 17, "said chlorination cartridge" should read --said chlorinator cartridge--

Signed and Sealed this
Twentieth Day of November, 2018

Andrei Iancu
*Director of the United States Patent and Trademark Office*

CERTIFICATE OF CORRECTION (continued)
U.S. Pat. No. 9,885,193 B2

Claim 18, "said chlorination cartridge" should read --said chlorinator cartridge--

Claim 19, "said replaceable cartridge" should read --said chlorinator cartridge--

Claim 20, "an authentication key, a processor" should read --an authentication key, and a processor--

Claim 25, "said controller" should read --a controller--